United States Patent [19]
Proctor

[11] Patent Number: 5,728,714
[45] Date of Patent: Mar. 17, 1998

[54] METHOD FOR TREATING HAIR LOSS USING TEMPO

[76] Inventor: Peter H. Proctor, 4126 SW. Freeway, Suite 1616, Houston, Tex. 77027

[21] Appl. No.: 465,416

[22] Filed: Jun. 5, 1995

Related U.S. Application Data

[63] Continuation-in-part of Ser. No. 229,374, Apr. 18, 1994, Pat. No. 5,470,876, and a continuation-in-part of Ser. No. 193,228, Feb. 7, 1994, Pat. No. 5,472,687, which is a continuation-in-part of Ser. No. 21,970, Feb. 24, 1993, Pat. No. 5,352,442, which is a continuation-in-part of Ser. No. 149,720, Jan. 29, 1988, abandoned, which is a continuation-in-part of Ser. No. 8,186, Jan. 28, 1987, abandoned, which is a continuation-in-part of Ser. No. 858,050, Apr. 30, 1986, abandoned, which is a continuation-in-part of Ser. No. 757,131, Jul. 18, 1985, abandoned.

[51] Int. Cl.$^6$ ............................................. A61K 31/445
[52] U.S. Cl. ........................... 514/315; 514/89; 514/327; 514/645
[58] Field of Search ...................... 514/315, 89, 327, 514/645

[56] References Cited

U.S. PATENT DOCUMENTS

| | | | |
|---|---|---|---|
| 2,409,754 | 10/1946 | Henze | 260/309.5 |
| 2,986,573 | 5/1961 | Topliss | 167/65 |
| 3,257,390 | 6/1966 | Patchett | 260/239.55 |
| 3,461,461 | 8/1969 | Anthony et al. | 260/256.4 |
| 3,527,864 | 9/1970 | MacMillen et al. | 424/177 |
| 3,551,554 | 12/1970 | Herschler | 424/7.1 |
| 3,896,238 | 7/1975 | Smith | 424/358 |
| 4,139,619 | 2/1979 | Chidsey, III | 424/45 |
| 4,184,039 | 1/1980 | Soldati | 544/12 |
| 4,254,145 | 3/1981 | Birnbaum | 424/305 |
| 4,344,941 | 8/1982 | Wiechert | 424/243 |
| 4,347,245 | 8/1982 | Shapiro | 424/241 |
| 4,367,227 | 1/1983 | Bingham | 424/243 |
| 4,444,762 | 4/1984 | Rajadhyaksha | 424/180 |
| 4,456,600 | 6/1984 | Wiechert | 424/238 |
| 4,596,812 | 6/1986 | Chidsey, III | 424/251 |
| 4,866,067 | 9/1989 | Di Schiena | 514/275 |
| 5,041,439 | 8/1991 | Kasting et al. | 514/227.2 |
| 5,120,831 | 6/1992 | Pickart | 530/331 |
| 5,177,061 | 1/1993 | Pickart | 514/18 |
| 5,214,032 | 5/1993 | Pickart | 514/16 |
| 5,252,559 | 10/1993 | Kronholm | 514/18 |
| 5,256,678 | 10/1993 | Nakaguchi | 514/356 |
| 5,462,946 | 10/1995 | Mitchell et al. | 514/315 |

FOREIGN PATENT DOCUMENTS

| | | | |
|---|---|---|---|
| 0027655 | 4/1981 | European Pat. Off. | 424/70 |
| 0249397 | 12/1987 | European Pat. Off. | |
| 0273202 | 7/1988 | European Pat. Off. | |
| 0327263 | 8/1989 | European Pat. Off. | |
| 0415598 | 3/1991 | European Pat. Off. | |
| 2198132 | 6/1988 | United Kingdom | |
| 8302558 | 8/1983 | WIPO | |
| 8600616 | 1/1986 | WIPO | |
| 8700427 | 1/1987 | WIPO | |
| 9113619 | 9/1991 | WIPO | |

OTHER PUBLICATIONS

Anderson, *Chemical Abstracts*, vol. 90, pp. 311K (1979).
Ando et al., *Chemical Abstracts*, 93:79872n (1980).
Bazzano et al., *Journal of American Academy of Dermatology*, vol. 15, pp. 880–883 (1986).
Barry, *Pharmacology of the Skin*, vol. 1, pp. 121–137 (1987).
Cheng et al., *Archives of Dermatological Research*, vol. 124, pp. 221–225 (1988).
Cumming et al., *Journal of American Medical Association*, vol. 247, pp. 1295–1298 (1982).
*Current Therapy*, pp. 599–603 (1984).
DeVillez, *Archives of Dermatology*, vol. 121, pp. 197–202 (1985).
Dostert et al., *Xenobiotica*, vol. 15, No. 10, pp. 799–803 (1985).
Ehman et al., *Investigative Radiology*, vol. 21, pp. 125–131 (1986).
Feelisch et al., *Evr. Journal of Pharmacology*, vol. 139, pp. 19–30 (1987).
Feelisch et al., *Evr. Journal of Pharmacology*, vol. 142, pp. 465–469 (1987).
Fox et al., *Annals of the New York Academy of Sciences*, vol. 411, pp. 14–19 (1983).
Goffman et al., *International Journal of Radiation, Oncology, Biology and Physics*, vol. 22, pp. 803–806 (Nov. 4, 1992).
Headington, *Current Therapeutic Research*, vol. 36, pp. 1098–1105 (1984).
Hearse et al., *Circulation Research*, vol. 60, pp. 375–383 (1987).
Herschler, *Chemical Abtstracts*, vol. 78, pp. 115239 (1973).
Ignarro et al., *Biochemica et. Biophysica Acta*, vol. 631, pp. 221–231 (1980).
Karlsson et al., *Journal of Cyclic Nucleotide and Protein Res.*, vol. 10, No. 4, pp. 309–315 (1985).
Kvedar, *Journal of American Academic Dermatology*, vol. 12 pp. 215–225 (1985).
*Longevity*, vol. 2, No. 3, p. 26 (Jan. 1988).
Lucky, *Archives of Dermatology*, vol. 121, pp. 55–56 (1985).
Messina, *Current Therapeutic Research*, vol. 34, pp. 319–324 (1983).
Messina, *Current Therapeutic Research*, vol. 38, pp. 269–282 (1985).
Mitchell et al., IBC USA Conference, South Natick, MA (Jun. 27, 1991).

(List continued on next page.)

*Primary Examiner*—Porfirio Nazario-Gonzalez
*Attorney, Agent, or Firm*—Daniel N. Lundeen; Sroufe, Payne & Lundeen, L.L.P.

[57] ABSTRACT

A method for ameliorating a cellular dysfunction of a tissue such as the cosmetic treatment of hair loss and stimulation of hair growth is disclosed. The method comprises administering substituted or unsubstituted 2,2,6,6-tetramethyl-1-piperdinyloxyl (TEMPO) to the affected tissue.

12 Claims, No Drawings

OTHER PUBLICATIONS

Mittal et al., *Proc. of National Academy of Science*, USA, vol. 74, No. 10, pp. 4360–4364 (1977).

Palmer et al., *Nature*, vol. 327, pp. 524–526 (Jun. 11, 1987).

Parrett et al., *Journal of Pharmacology*, vol. 91, pp. 49–59 (1987).

Proctor et al., *Physiological Chemistry and Physics in Medical NMR*, vol. 16, pp. 175–195 (1984).

Shapiro et al., *Journal of Clinical Endocrinology and Metabolism*, vol. 51, pp. 429–430 (1980).

Stewart, *International Journal of Dermatology*, vol. 17, pp. 167–179 (1978).

Thompson, *Federal Drug Administration Consumer*, pp. 10 and 12 (Mar. 10, 1981).

Tiffany–Castiglion, *Biochemical Pharmacology*, vol. 31, No. 2, pp. 181–188 (1982).

Torre (Ed.), *Annals of the New York Academy of Sciences*, vol. 411, Table of Contents (1983).

Vermorken, *Acta Dermatovener*, (Stockholm), vol. 63, pp. 268–269 (1982).

Voorhees (Ed.), *Dermatologica*, vol. 175, suppl. 2, pp. 1–56 (1987).

Watanabe et al., *Archives of Dermatological Research*, vol. 278, pp. 470–473 (1986).

Weissmann, *Archives of Dermatology*, vol. 121, pp. 57–62 (1985).

Yoshioka et al. *Archives of Dermatological Research*, vol. 278, pp. 177–183 (1986).

Proctor, *Archives of Dermatology*, p. 1146 (Aug. 1989).

Gelvan et al., *Proc. of National Academy of Science*, USA, vol. 88, pp. 4680–4684 (1991).

Samuni et al., *Journal of Clinical Investigation*, vol. 87, pp. 1526–1530 (1991).

Samuni et al., *Biochemistry*, vol. 30, pp. 555–561 (1991).

Ignarro et al., *J. Bio. Chem.*, 261(11), pp. 4997–5002 (1986).

METHOD FOR TREATING HAIR LOSS USING TEMPO

CROSS-REFERENCE TO RELATED APPLICATIONS

This application is a continuation-in-part of application Ser. No. 08/229,374, filed Apr. 18, 1994, now U.S. Pat. No. 5,470,876 and Ser. No. 08/193,228, filed Feb. 7, 1994, now U.S. Pat. No. 5,472,687, which are continuations-in-part of Ser. No. 08/021,970, filed Feb. 24, 1993, now U.S. Pat. No. 5,352,442; which is a continuation-in-part of Ser. No. 07/149,720, filed Jan. 29, 1988, abandoned; which is a continuation-in-part of application Ser. No. 07/008,186, filed Jan. 28, 1987, abandoned; which is a continuation-in-part of application Ser. No. 06/858,050, Apr. 30, 1986, abandoned; which is a continuation-in-part of application Ser. No. 06/757,131, Jul. 18, 1985, abandoned.

FIELD OF THE INVENTION

This invention relates to a method for treating hair loss using 2,2,6,6-tetramethyl-1-piperidinyloxyl (TEMPO).

BACKGROUND OF THE INVENTION

Several compounds have recently gained recognition for ameliorating cellular dysfunction. One type of dysfunction which has been well studied is alopecia for which anti-alopecia agents such as minoxidil and cyoctol have gained attention. However, most of these anti-alopecia agents are only minimally effective in some cases and/or can cause adverse dermatological or systemic reactions. Thus, the search continues for new, safer and more effective anti-alopecia agents as well as agents useful for treating other dysfunctionalities.

SUMMARY OF THE INVENTION

Applicant has discovered that 2,2,6,6-tetramethyl-1-piperidinyloxyl (TEMPO) can inhibit free radicals in the tissue to which it is administered. TEMPO has properties in the body for ameliorating certain cellular dysfunctions in tissue attributed, in part, to high energy oxygen and hydroxyl free radicals, and enhancing recuperation of the tissue. 2,2,6,6-Tetramethyl-1-piperidinyloxyl can be administered, for example, as an anti-alopecia agent to stimulate cosmetic hair growth, or as a protectant to minimize hair loss during cancer treatments known to induce hair loss.

DETAILED DESCRIPTION OF THE INVENTION

In the present invention, 2,2,6,6-tetramethyl-1-piperidinyloxyl (TEMPO) is compounded in a pharmaceutical formulation or carrier for topical or internal administration. The topical pharmaceutical carrier in which the TEMPO is generally substantially homogeneously dispersed can be an aqueous dispersion or suspension, or a water-in-oil or oil-in-water emulsion depending on the administration route. Topical pharmaceutical carriers which can be mentioned include water, urea, alcohols and glycols such as methanol, ethanol, propanol, butanol, ethylene glycol, propylene glycol, and the like. Internally administered pharmaceutical carriers typically include a sterile vehicle such as water or ethanol in which the TEMPO is suspended, dispersed or dissolved.

Suitable water-in-oil emulsions are commercially available under the designations Aquaphor, cold cream, Eucerin, hydrous lanolin, Hydrosorb hydrophilic petrolatum, Nivea, Polysorb, Qualatum and Velvachol. Suitable oil-in-water emulsions are available commercially under the designations acid mantle cream, Almay emulsion cream, Cetaphil, Dermabase, Dermavan, hydrophilic ointment, Keri cream, Lubriderm cream, Multibase cream, Neobase cream, Unibase cream, Vanibase cream and Wibi. The carrier may further contain various other emollients, emulsifiers, water, perfumes, colorants, preservatives, and the like. The topical formulation is in the form of a cream, lotion, shampoo, cream rinse, or the like.

TEMPO is a stable nitroxide radical which is a commercially available spin label. TEMPO can be unsubstituted or substituted, typically in the 4 position, for example, 4-amino, 4-(2-bromoacetamido), 4-(ethoxyfluorophosphonyloxy), 4-hydroxy, 4-(2-iodoacetamido), 4-isothiocyanato, 4-maleimido, 4-(4-nitrobenzoyloxyl), 4-oxo, 4-phosphonooxy, and the like.

Effective amounts of the TEMPO generally range from about 0.01 to about 20% by weight of the administered composition, more preferably from about 0.1 to about 10% by weight, most preferably from about 0.5 to about 3% by weight, but more or less can be present in the composition depending on the particular TEMPO formulation and the treatment conditions.

The TEMPO can be used alone or in combination with other additaments which are available to enhance the function of hair growth stimulation such as, for example, the hydroxyl radical scavengers, antiandrogens and others described in International Publication No. WO 87/00427 (International Application No. PCT/US86/01393) published on Jan. 29, 1987; and European Patent Application No. 89300785.6, Publication No. 0327263/A1, published Aug. 9, 1989; both of which are hereby incorporated in their entirety herein as though fully set forth verbatim, including reference therein to the publication of Ross & Ross, "Selected Specific Rates of Reactions of Transients From Water In Aqueous Solution. III. Hydroxyl Radical and Pure Hydroxyl Radicals and Their Radical Ions," National Standard Reference Data Series, National Bureau of Standards, 59 (1977), which is also incorporated herein by reference.

According to the present invention, the TEMPO can be administered to the skin to be treated, such as the scalp. Depending on the type of hair loss or alopecia being treated and the conditions thereof, the stimulation of hair growth can usually be obtained by topical application, preferably repeated daily application for a period of 3–6 months. The utility of topically applied TEMPO is not limited thereto, however, and the stimulation of hair growth can include an increased rate of growth, increased hair diameter, follicular neogenesis, and the like; inhibiting hair loss or alopecia from progressing, for example, in male pattern baldness, or during the course of treatment with other therapeutic agents known to induce hair loss, such as chemotherapy or radiation therapy in cancer treatment; as well as, ameliorating the rate of protein oxidation, DNA scission, cell viability loss, and the like in the tissue of internal organs such as the heart and brain; and ameliorating capillary loss, tissue atrophy characterized by a decrease in collagen and/or elastin and a decreased number, size and reproduction potential of fibroblasts, and strengthening the dermal-epidermal junction in skin; ischemic reperfusion injury secondary to myocardial infarction, stroke and surgical procedures; wound healing, for example, in burns and diabetic ulcerations; inflammatory and degenerative diseases such as rheumatoid arthritis, lupus and the like; fibrotic diseases such as Peyronie's disease, scarring, pulmonary fibrosis, and vitreous fibrosis; prevention of free-radical-induced vascular damage such as in atherosclerosis; other free radical diseases as outlined in Proctor et al., "Free Radicals and Disease in Man," *Physiological Chemistry and Physics and Medical NMR,* volume 16, pp. 175–195 (1984) which is hereby incorporated herein by reference; and the like.

The invention is illustrated by way of the following examples:

EXAMPLE 1

A TEMPO shampoo is prepared by mixing 0.5 g of 4-hydroxy-TEMPO in 500 ml of a commercially available shampoo. The shampoo is used daily on the scalp for normal shampooing of the hair for a period of from 3 to 6 months to obtain cosmetic hair growth.

EXAMPLE 2

A solution of TEMPO is prepared and used in the course of radiation treatment. 4-Hydroxy-TEMPO, obtained commercially from Aldrich Chemical Company, is dissolved in 70 percent ethanol/30 percent water at a concentration of 70 mg/ml. Topical application of the solution is made prior to irradiation exposure at 20Gy to 50Gy. Hair loss in the treated TEMPO subjects is less severe and returns to normal more rapidly than in the control group similarly treated with the same ethanol/water solution without TEMPO. Skin samples obtained from the treated group test positive for the presence of 4-hydroxy-TEMPO, while other tissue and blood specimens generally test negative. The application of the solution can also continue daily after the irradiation exposure. See Goffman, et al., "Topical Application of Nitroxide Protects Radiation-Induced Alopecia in Guinea Pigs," International Journal of Radiation Oncology, Biology and Physics, Volume 22, pp. 803–806, 1992, which is hereby incorporated herein by reference.

EXAMPLE 3

A 0.4 or 1 mM solution of TEMPO is used to significantly reduce cardiac injury caused by reperfusion arrhythmia-ventricular fibrillation and ventricular tachycardia, as well as, post ischemic release of lactate dehydrogenase and OH-formation in isolated rat heads subjected to regional ischemia. The rat heads are obtained and perfused using a modified Krebs-Henseleit (KH) buffer, as detailed in Gelvan et al., "Cardiac Reperfusion Damage Prevented by a Nitroxide Free Radical," *Proceedings of the National Academy of Sciences,* USA, Medical Sciences, Vol. 88, pp. 4680–4684, June 1991, which is hereby incorporated herein by reference, in which the TEMPO solution was added to the perfusate. After reperfusion, head function and resulting damage is analyzed. TEMPO is found to strongly protect against reperfusion injury by preventing OH-formation rather than by decreasing heart rate or by direct suppression of arrhythmia.

The invention is described above and illustrated herein with reference to specific chemical formulas, preparations and therapeutic and cosmetic applications. Many variations and modifications will become apparent to those skilled in the art in view of the foregoing disclosure. It is intended that the following claims are not to be limited thereby, and are to be construed in accordance with the spirit and scope thereof.

I claim:

1. A method for inhibiting the activity of hydroxyl and oxygen free radicals in tissue of an organism, comprising the step of:

administering substituted or unsubstituted 2,2,6,6-tetramethyl-1-piperidinyloxyl to the tissue in an effective amount to inhibit the free radicals.

2. The method of claim 1, whereto the administration step is topical.

3. The method of claim 2, wherein the 2,2,6,6-tetramethyl-1-piperdinyloxyl is in the form of a dispersion, suspension or emulsion selected from creams, lotions, shampoos and cream rinses.

4. The method of claim 3, wherein the dispersion, suspension or emulsion comprises from about 0.01 to about 20 percent by weight of said piperidinyloxyl.

5. The method of claim 1, wherein the 2,2,6,6-tetramethyl-1-piperidinyloxyl includes a substituent selected from 4-amino; 4-(2-bromoacetamido); 4-(ethoxyfluorophosphonyloxy); 4-hydroxy; 4-(2-iodoacetamido); 4-maleimido; 4-(4-nitrobenzoyloxyl); 4-oxo; and 4-phosphonooxy.

6. The method of claim 1, wherein the administration step is internal.

7. A method for stimulating hair growth, comprising the step of:

administering an effective amount of substituted or unsubstituted 2,2,6,6-tetramethyl-1-piperdinyloxyl to the affected area.

8. The method of claim 7, wherein the administration step is topical.

9. The method of claim 8, wherein the 2,2,6,6-tetramethyl-1-piperidinyloxyl is in the form of a dispersion, suspension or emulsion selected from creams, lotions, shampoos and cream rinses.

10. The method of claim 7, wherein the 2,2,6,6-tetramethyl-1-piperidinyloxyl includes a substituent selected from 4-amino; 4-(2-bromoacetamido); 4-(ethoxyfluorophosphonyloxy); 4-hydroxy; 4-(2-iodoacetamido); 4-maleimido; 4-(4-nitrobenzoyloxyl); 4-oxo; and 4-phosphonooxy.

11. The method of claim 9, wherein the dispersion, suspension or emulsion comprises from about 0.01 to about 20 percent by weight of said piperidinyloxyl.

12. A method for inhibiting the activity of hydroxyl and oxygen free radicals in tissue of an organism, comprising the step of:

administering a dispersion, suspension or emulsion of from about 0.01 to about 20 percent by weight of substituted or unsubstituted 2,2,6,6-tetramethyl-1-piperidinyloxyl to the tissue.

* * * * *

UNITED STATES PATENT AND TRADEMARK OFFICE
CERTIFICATE OF CORRECTION

PATENT NO.    : 5,728,714
DATED         : March 17, 1998
INVENTOR(S)   : Proctor It is certified that error appears in the above-indentified patent and that said Letters Patent is hereby corrected as shown below:

Column 3, line 52: the term "head function" should read --heart function--.

Column 4, in claim 2, line 1: the word "whereto" should read --wherein--.

Signed and Sealed this

Twenty-first Day of July, 1998

Attest:

BRUCE LEHMAN

Attesting Officer    Commissioner of Patents and Trademarks